United States Patent
Beau (10) Patent No.: US 9,581,537 B2
(45) Date of Patent: Feb. 28, 2017

(54) TESTBENCH DEVICE, IN PARTICULAR TRIBOMETER, FOR PISTON RING/CYLINDER RUNWAY SYSTEMS

(71) Applicant: MAN Truck & Bus AG, Munich (DE)

(72) Inventor: Patrick Beau, Nuremberg (DE)

(73) Assignee: MAN TRUCK & BUS AG, Munich (DE)

( * ) Notice: Subject to any disclaimer, the term of this patent is extended or adjusted under 35 U.S.C. 154(b) by 148 days.

(21) Appl. No.: 14/495,028

(22) Filed: Sep. 24, 2014

(65) Prior Publication Data
US 2015/0082860 A1   Mar. 26, 2015

(30) Foreign Application Priority Data
Sep. 26, 2013 (DE) .................. 10 2013 016 004

(51) Int. Cl.
  *G01N 3/56* (2006.01)
  *G01N 19/02* (2006.01)
  *G01M 13/00* (2006.01)

(52) U.S. Cl.
  CPC ............ *G01N 19/02* (2013.01); *G01M 13/005* (2013.01); *G01N 3/56* (2013.01)

(58) Field of Classification Search
  CPC ..... G01M 13/005; G01M 99/007; G01N 3/56; G01N 19/02
  USPC ............................................. 73/7, 9, 114.78
  See application file for complete search history.

(56) References Cited

U.S. PATENT DOCUMENTS

| | | | | |
|---|---|---|---|---|
| 4,657,228 A | * | 4/1987 | Lautzenhiser | ........ F16F 9/0236 188/322.14 |
| 5,007,284 A | * | 4/1991 | Slone | .................. G01M 13/005 73/114.78 |
| 6,622,571 B2 | * | 9/2003 | Chen | ........................ G01N 3/08 73/826 |

FOREIGN PATENT DOCUMENTS

DE   10 2009 008 272 A1   8/2010

* cited by examiner

*Primary Examiner* — Justin Olamit
(74) *Attorney, Agent, or Firm* — Lucas & Mercanti, LLP (57) ABSTRACT

A testbench device for the analysis and/or optimization of tribological properties in a piston ring/cylinder runway system, includes a cylinder segment-holding device for holding a cylinder runway segment as a testpiece, and a piston ring-holding device holding at least one piston ring element and capable of bringing the at least one piston ring element into bearing contact with the cylinder runway segment. An actuation device actuates the cylinder runway segment and/or the piston ring element such that relative displacement with respect to one another takes place in at least one defined direction of space, in particular in the form of an oscillating movement. The piston ring-holding device has a piston having a ring-shaped outer contour and with at least one circumferentially continuous piston ring groove, in which a piston ring is held as a piston ring element.

21 Claims, 5 Drawing Sheets

TESTBENCH DEVICE, IN PARTICULAR TRIBOMETER, FOR PISTON RING/CYLINDER RUNWAY SYSTEMS

CROSS-REFERENCE TO RELATED APPLICATIONS

This application claims the priority of DE 10 2013 016 004.9 filed Sep. 26, 2013, which is incorporated by reference herein.

BACKGROUND OF THE INVENTION

The invention relates to a testbench device, in particular a tribometer.

For a substantial and, in particular, effective analysis or optimisation of friction systems, tribometers, as they are known, are regularly used. Tribometers are testbenches developed especially for investigating tribological variables, such as, for example, friction, wear or lubrication. In vehicle development, above all, the optimisation of the most diverse possible friction systems constitutes an essential area of development in order to utilise the potential of optimisations relating to efficiency and to service life and in order to satisfy future requirements. In particular the piston group/cylinder runway friction system plays an important part in this context, since up to 50 percent of the overall friction losses of an internal combustion engine may occur here.

DE 10 2009 008 272 A1 discloses a tribometer testbench, by means of which friction and wear between a cylinder runway segment, produced, for example, from a cylinder crankcase or from a cylinder liner, and a piston ring or a piston ring segment can be measured. The piston ring is fastened here to a sturdy fixed holder. The cylinder runway segment, capable of being brought into bearing contact with the piston ring, is fastened to a travelling slide which can be moved back and forth in oscillation in a defined direction in relation to the holder and with a defined stroke. As a result of the movement of the cylinder runway segment in relation to the piston ring, the processes in an internal combustion engine are thus to be simulated. Furthermore, the travelling slide has a heating element that can heat the cylinder runway segment to a defined temperature. Moreover, the cylinder runway segment can be pressed against the piston ring with a defined pressure force by means of weights. Using the heating element and the weights, simulation is to be made increasingly close to reality. However, such a tribometer testbench nevertheless has the disadvantage that the reproducibility of the simulation results and, in particular, also the transferability of the simulation results to a real internal combustion engine system are greatly restricted.

BRIEF SUMMARY OF THE INVENTION

An object of the invention is to provide a testbench device, in particular a tribometer, in which the reproducibility of the simulation results and/or the transferability of the simulation results to the real internal combustion engine system are/is improved in a simple way.

The invention relates to a testbench device, in particular a tribometer, for the analysis and/or optimisation of the tribological properties in a piston ring/cylinder runway system. A cylinder runway segment is held on a cylinder segment-holding device as a testpiece. In addition, at least one piston ring element is held on a piston ring-holding device and capable of being brought into bearing contact with the cylinder runway segment. Further, an actuation device is provided, by means of which the cylinder runway segment and/or the piston ring element can be actuated in such a way that relative displacement with respect to one another takes place in at least one defined direction of space, in particular in the form of an oscillating movement. According to the an embodiment of invention, the piston ring-holding device has a piston having a ring-shaped outer contour and with at least one circumferentially continuous piston ring groove, in which a piston ring is arranged and/or inserted as a piston ring element.

By a complete piston ring being arranged and/or inserted in the circumferentially continuous piston ring groove of the piston, simulation results especially close to reality can be obtained by means of the testbench device according to the invention, since abstraction is markedly reduced, as compared with a real system.

Preferably, the piston ring element arranged and/or introduced in the piston ring groove is guided in the piston ring groove with a defined axial play, so that the piston ring can also execute what is known as a "twisting movement" in the piston ring groove, such as regularly occurs under real conditions.

In one embodiment, the piston ring-holding device has a cylinder element which at least partially surrounds the piston in the circumferential direction and which is in bearing contact by its cylinder running face with the piston ring element, the cylinder element and the piston being secured in such a way that relative movement between the cylinder element and the piston is prevented. Thus, the piston ring element can be supported on the cylinder running face and the simulations are made increasingly close to reality. Preferably, the cylinder element may surround the piston completely in a ring-shaped manner, so that the piston can be supported over its entire circumference on the cylinder running face and realistic piston ring tangential forces can be copied.

In another embodiment, the cylinder element and the piston may be secured to a parallelepipedal reception block of the piston ring-holding device, and the reception block may have a measuring device, by means of which a coefficient of friction between piston ring and to the cylinder runway segment can be determined. Such a set-up makes it possible to determine the coefficient of friction reliably and accurately.

In a further embodiment, the cylinder element may have a window-like cylinder element recess providing free access from outside to the piston ring element, the cylinder element recess being designed and/or arranged in such a way that the cylinder runway segment held on the cylinder segment-holding device can be brought through the cylinder element recess into bearing contact with the piston ring element and can be displaced in relation to the piston ring element in defined directions of space. By means of the window-like cylinder element recess, the cylinder runway segment can be brought into bearing contact with the piston ring element in a simple way.

In a preferred embodiment, a lubrication device is provided, by means of which a defined quantity of lubricant, in particular lubricating oil, can be delivered at least to the contact regions of the piston ring element, piston ring groove and cylinder runway segment. Lubrication of these contact regions which is close to reality can thereby be achieved. Preferably, the defined delivery quantity of lubricant may amount to about 2.5 microliters per minute, in order to copy a deficient lubrication state, such as occurs, for example, at the top dead centre of a piston.

The piston may have a lubricant duct which is fluidically connected to the piston ring groove through which the lubricant can be conveyed into the at least one piston ring groove. The lubricant temperature in the lubricant duct can thereby be adapted to the piston temperature. Preferably, the at least one piston ring groove may be formed by two ring lands spaced apart from one another and the lubricant duct may issue into at least one of these ring lands by means of an issue port towards the piston ring groove. The lubricant can be conveyed directly to the piston ring element by means of the issue port issuing towards the piston ring groove.

According to a further embodiment, a piston heating element, in particular a heating cartridge, is provided, by means of which the piston can be heated to a defined temperature, in particular to about 350 degrees Celsius. Moreover, a cylinder runway segment beating element, in particular a heating foil, may be provided, by means of which the cylinder runway segment can be heated to a defined temperature, in particular to about 130 degrees Celsius. The simulations can be made increasingly close to reality by the piston heating element and/or the cylinder runway heating element.

In a concrete embodiment, the reception block is arranged at least partially in an inner cavity of the piston designed as a hollow piston, the reception block being secured to the piston by an adapter element arranged between reception block and piston, and the piston heating element being secured to the reception block in such a way that the heating warmth of the piston heating element passes into the piston via the reception block and the adapter element. Especially effective heating of the piston is thereby made possible.

In a another embodiment, the cylinder segment-holding device has a testpiece holder and a testpiece stay which is secured to the testpiece holder and to which the cylinder runway segment is secured, the testpiece stay being secured to the testpiece holder pivotably and/or rotatably, in such a way that an angular offset between a cylinder segment axis running in the axial direction of the cylinder runway segment and a piston ring element axis running in the axial direction of the piston ring element can be compensated and/or set. By the angular offset being compensated and/or set, a contact region between piston ring element and cylinder runway segment can be optimised.

A blocking arrangement may be provided, by means of which the pivoting and/or the rotation of the testpiece stay in relation to the testpiece holder can be blocked and released. By means of the blocking arrangement, reliable blocking and release of the pivoting and/or rotation of the testpiece stay in relation to the testpiece holder become/becomes possible. Preferably, the blocking arrangement may have one or more screw elements, in particular spherical pressure screws, which can be screwed into the testpiece holder and/or into the testpiece stay in order to block pivoting and/or rotation. Pivoting and/or rotation can thereby be blocked in an especially simple way.

In a further preferred embodiment, the testpiece stay is of U-shaped form, the cylinder runway segment, manufactured particularly in the manner of a cylinder crankcase, being arranged between the U-legs of the testpiece stay and/or being secured to the U-legs of the testpiece stay. By virtue of this type of construction, in particular, thick-walled cylinder runway segments can be secured to the cylinder segment-holding device in a simple way.

In an alternative embodiment, the testpiece stay has a bearing region contour-adapted to a side, facing away from the piston ring element, of the cylinder runway segment, manufactured particularly in the manner of a cylinder liner, in which case, to secure the cylinder runway segment to the testpiece stay, the cylinder runway segment can be clamped against the bearing region by at least one clamping element, in particular a clamping jaw. As a result, in particular, thin-walled cylinder runway segments can be secured reliably to the testpiece stay.

A pressing device may be provided, by means of which the cylinder runway segment can be pressed against the piston ring element with a defined pressure force. By means of the pressing device, the simulations carried out by means of the testbench device according to the invention can be varied and optimised.

According to another embodiment, the cylinder segment-holding device is designed in such a way that the setting and/or compensation of the angular offset take place/takes place by the cylinder runway segment being pressed against the piston ring element with the defined pressure force. The angular offset can be set and/or compensated especially simply in this way. Preferably, the testpiece holder may have a cylindrical recess, in which a cylindrical pin of the testpiece stay is guided with a radial play enabling the angular offset to be set and/or compensated. This makes it possible to set and/or compensate the angular offset especially simply.

In a preferred embodiment, the cylinder runway segment is arranged above the piston ring element in a vertical axis direction. Thus, the cylinder runway segment is capable of being brought by a bearing region into bearing, contact with the piston ring element, the cylinder runway segment being secured to the cylinder segment-holding device in such a way that the bearing region is displaced in the axial direction of the cylinder runway segment as a result of the rotation of the cylinder runway segment through 180 degrees about a vertical axis running in the vertical axis direction. A single cylinder runway segment can thereby be used for two test runs.

A tilting device may be provided, by means of which the cylinder segment-holding device, together with the piston ring-holding device, can be tilted from a horizontal to a vertical position, and vice versa, in which case, in the horizontal position, a piston axis running in the piston axial direction runs horizontally and, in the vertical position, the piston axis runs vertically. Thus, the testbench device can be mounted and adjusted in the horizontal position and simulations close to reality can be carried out in the vertical position.

In a preferred embodiment, the piston ring-holding device may be held stationarily and, by means of the actuation device, the cylinder segment-holding device may be displaced in relation to the stationary piston ring-holding device in the defined directions of space, in particular in the piston axial direction. Relative movement between cylinder runway segment and piston ring element can thereby be implemented in an especially simple way.

The advantageous embodiments and/or developments of the invention which are explained above and/or are reproduced in the subclaims may be employed individually or else in any combination with one another, except, for example, in cases of unequivocal dependencies or incompatible alternatives.

BRIEF DESCRIPTION OF THE DRAWINGS

The invention and its advantageous refinements and/or developments and also the advantages thereof are explained, merely by way of example, hereafter with reference to the drawings in which.

DETAILED DESCRIPTION OF THE PREFERRED EMBODIMENTS

Figure 1:
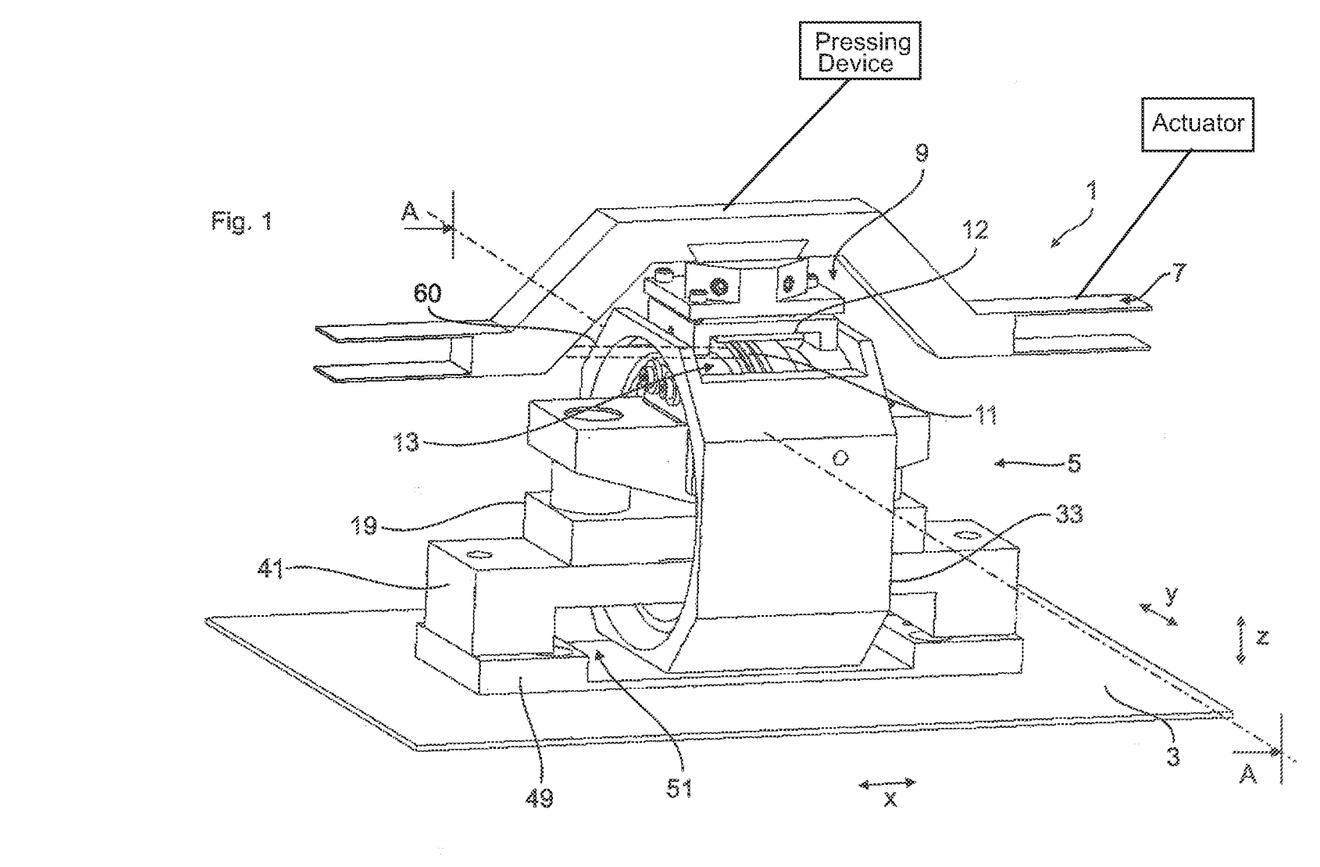
FIG. 1 is a perspective view of an exemplary embodiment of a testbench device according to the invention.
Figure 9:
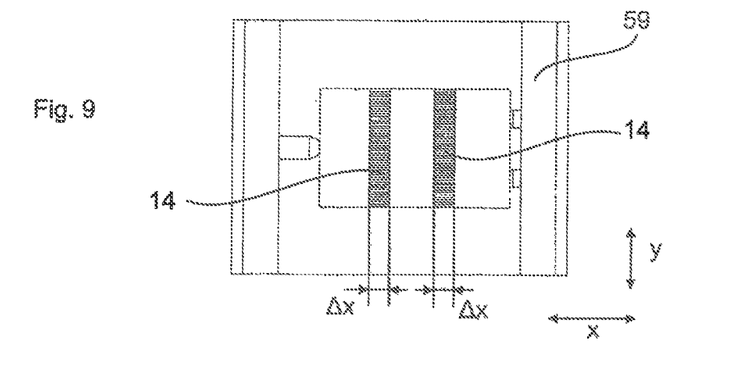
FIG. 9 is a bottom view of the cylinder segment-holding device according to FIG. 7.

FIG. 1 shows a testbench device 1 simulating close to reality a piston ring/cylinder runway system. The testbench device 1 has a piston ring-holding device 5 secured to a fixing plate 3 and a cylinder segment-holding device 9 secured to a rocker 7. The rocker 7, arranged above the fixing plate 3 so as to be spaced apart in the vertical axis direction is displaceable in the longitudinal axis direction x in relation to the fixed fixing plate 3 by means of an actuation device, not shown in the figures. A complete piston ring 11 is held on the piston ring-holding device 5, while a cylinder runway segment 12 (FIG. 2) manufactured in the manner of a crankcase is held on the cylinder segment-holding device 9. For simulations of the real processes in the piston ring/cylinder runway system, the cylinder runway segment 12 can be brought into bearing contact with the piston ring 11 by means of the actuation device and be displaced in relation to the piston ring 11. The displacement of the cylinder runway segment 12 in relation to the piston ring 11 preferably takes place in the form of an oscillating movement over a defined distance, with the result that a friction track 14 with a track width Δx (FIG. 9) is formed on the cylinder runway segment 12.

Figure 2:
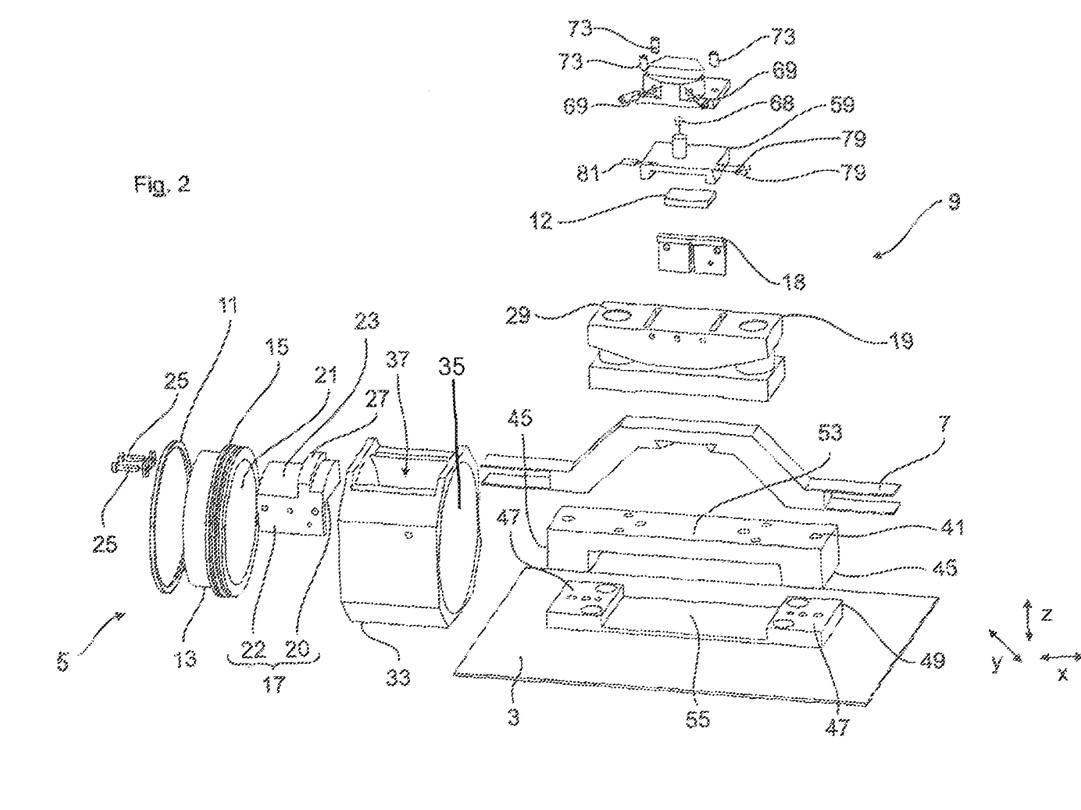
FIG. 2 shows the components of the testbench device according to FIG. 1 in an exploded illustration.
Figure 3:
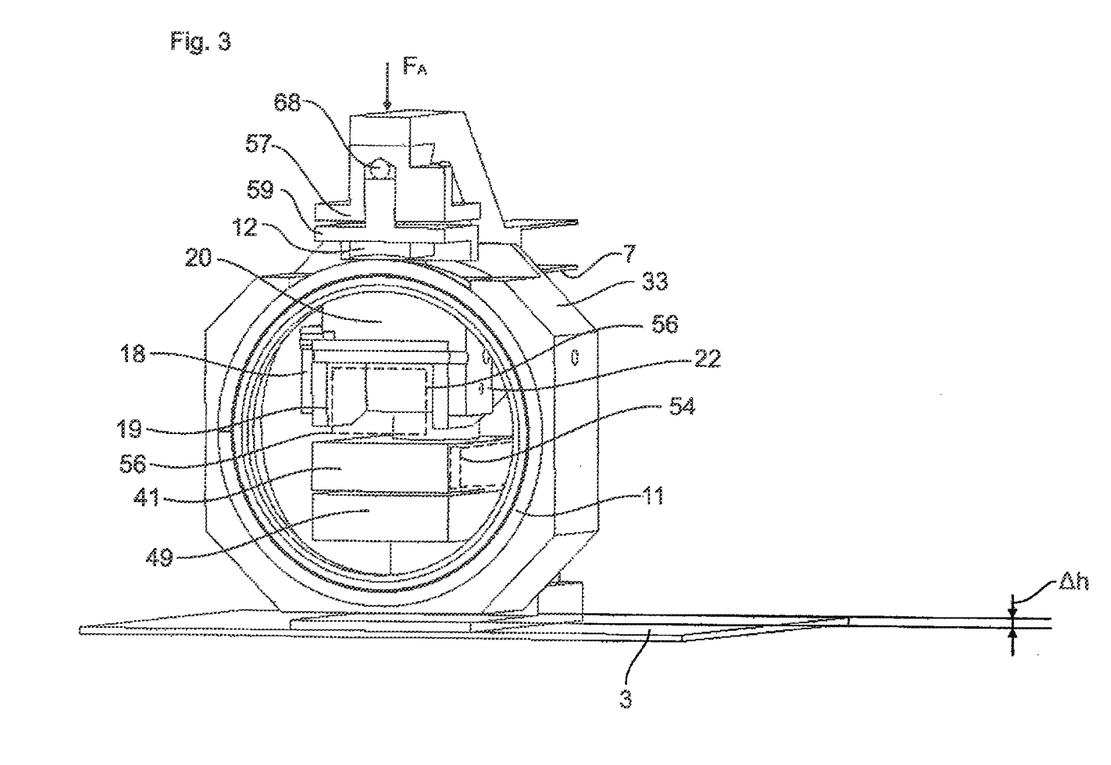
FIG. 3 is a sectional view along the sectional plane A-A of FIG. 1.

The detailed set-up of the piston ring-holding device 5 and of the cylinder segment-holding device 9 may be gathered from FIG. 2. The piston ring-holding device 5 has a ring-shaped piston adaptation 13 manufactured from a piston and having a circumferentially completely continuous piston ring groove 15 into which the piston ring 11 can be inserted. The piston adaptation 13 can be secured to a parallelepipedal reception block 19 of the piston ring-holding device 5 by means of an adapter element 17 and by means of a plate-shaped abutment 18. The adapter element 17 consists here, for example, of an adapter body 20 and a plate-shaped leg 22 arranged on the outside of the adapter body 20 in a transverse axis direction y and projecting downwards from the adapter body 20 in the vertical axis direction z. To secure the piston adaptation 13 to the adapter element 17, the ring-shaped piston adaptation 13 is brought with its inner face 21 into sheet-like bearing contact with a bearing face 23, contour-adapted to the inner face 21, of the adapter body 20 and is clamped by means of a plurality of, here two, screws 25 against a land 27 of the adapter body 20, the said land 27 projecting upwards from the bearing face 23 in the vertical axis direction z. Further, the plate-shaped abutment 18 is tied, opposite to the leg 22, to the outside of the adapter body 20 in a transverse axis direction y and, together with the said adapter body and the leg 22, forms a U-shaped set-up (FIG. 3). The adapter body 20, as seen in the vertical axis direction z, has at the bottom a planar bearing face which can be brought into sheet-like bearing contact with a topside 29 of the parallelepipedal reception block 19. The securing of the adapter element 17, bearing with the bearing face against the reception block 19, to the reception block 19 takes place here, for example, by means of three screw connections (FIG. 2) which are led through the leg 22, through the abutment 18 tied to the adapter element 17 and through the reception block 19 and which run in the transverse axis direction y.

FIG. 2 shows, further, a cylinder adaptation 33 of the piston ring-holding device 5, the said cylinder adaptation being likewise securable to the reception block 19 and surrounding the piston completely in a ring-shaped manner. As shown in FIG. 3, the cylinder adaptation 33 secured to the reception block 19 is in bearing contact by means of its cylinder running face 35 with the piston ring 11. The cylinder adaptation 33 has at the top, as seen in the vertical axis direction z, a window-like recess 37 (FIG. 2) providing free access from outside to the piston ring 11. Via this window-like recess 37, the cylinder runway segment 12 held on the cylinder segment-holding device 9 can be brought into bearing contact with the piston ring 11 and therefore be displaced in relation to the piston ring 11 in the longitudinal axis direction x.

It may be gathered, further, from FIG. 1 that the reception block 19 lies on a here U-shaped intermediate plate 41 or is screwed to the intermediate plate 41. According to FIG. 2, the intermediate plate 41 has, at its and regions projecting from the cylinder adaptation 33 in the longitudinal axis direction x, U-legs 45 which project downwards in the vertical axis direction z and which are in bearing contact with U-legs 47, projecting upwards in the vertical axis direction z, of a U-shaped baseplate 49 arranged beneath the intermediate plate 41 in the vertical axis direction z. The intermediate plate 41 and the baseplate 49 are screwed to one another at their U-legs 45 and 47 and form a free space 51 (FIG. 1), through which the piston adaptation 13, the piston ring 11 and the cylinder adaptation 33 are led. According to FIG. 3, a U-base 53 of the intermediate plate 41 and a U-base 55 of the baseplate 49 are spaced apart from one another, in such a way that the cylinder adaptation 33 is out of bearing contact with the U-base 55 of the baseplate 49 with a height offset Δh (FIG. 3). Since the cylinder adaptation 33 is out of bearing contact with the baseplate 49, it is possible to determine accurately a coefficient of friction between the piston ring 11 and the cylinder runway segment 12 by a measuring device 54 provided on the reception block 19 and indicated in FIG. 3 by dashed lines. Furthermore, the baseplate 49 is in bearing contact on the underside in a vertical axis direction z with the fixing plate 3 and is fastened to the fixing plate 3 by means of screw connections.

Further, the reception block 19 may have a heating cartridge 56, indicated in FIG. 3 by dashed lines, by means of which the piston adaptation 13 can be heated to a defined temperature, for example to about 350° C. In order to ensure as high an introduction of heat as possible into the piston adaptation 13, as already mentioned, the parallelepipedal reception block 19 with the adaptation element 17 and the adaptation element 17 with the piston adaptation 13 bear one against the other in a sheet-like bearing connection. Moreover, the piston ring-holding device 5 may have a lubrication device, at which FIG. 1 shows merely a conveying line 60 issuing into the piston ring groove 15 as indicated by dashed lines. By means of the lubrication device, a defined quantity of lubricating oil, for example 2.5 microliters per minute, can be conveyed into the piston ring groove 15.

As illustrated in FIGS. 2 and 3, the cylinder segment-holding device 9 comprises, further, a testpiece holder and a testpiece stay 59 securable to a testpiece holder 57 by means of a fastening device 58 (FIG. 4) and holding the cylinder runway segment 12.

Figure 5:
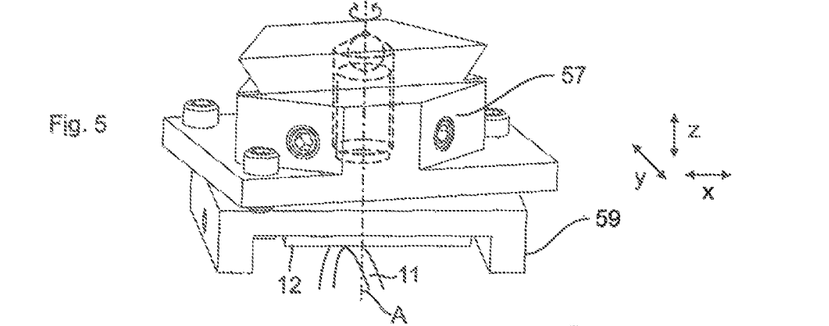
FIG. 5 is a perspective view of a first degree of freedom of the cylinder segment-holding device of FIG. 4.
Figure 6:
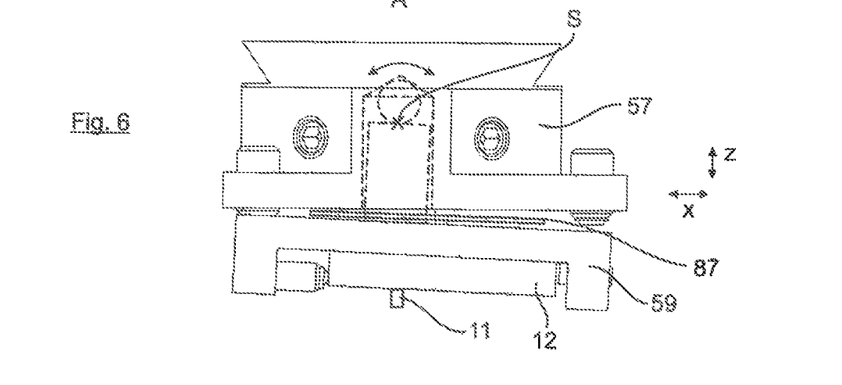
FIG. 6 is a side view to illustrate a second degree of freedom of the cylinder segment-holding device of FIG. 4.

The fastening device 58 is designed in such a way that the testpiece stay 59 secured to the testpiece holder 57 is rotatable (FIG. 5) in relation to the testpiece holder 57 about an axis A running in the vertical axis direction and is pivotable (FIG. 6) about a pivoting point S. The rotation and the pivoting of the testpiece stay 59 in relation to the testpiece holder 57 make it possible to compensate an angular offset between a cylinder segment axis running in the axial direction of the cylinder runway segment and a piston ring axis running in the axial direction of the piston ring.

Figure 4:
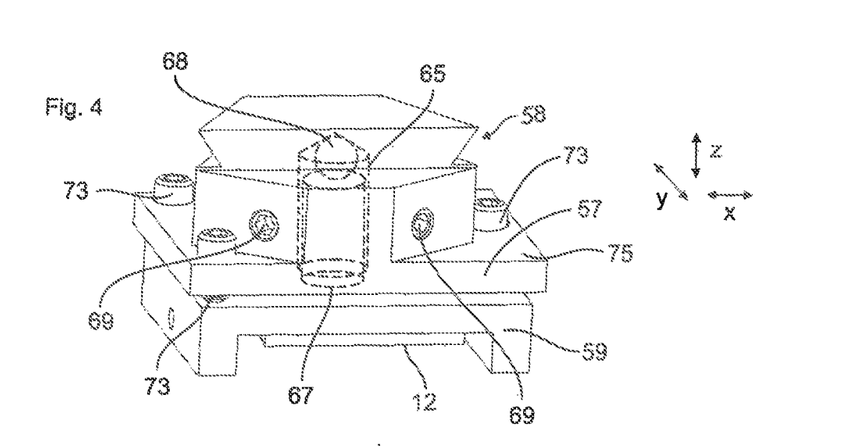
FIG. 4 is a perspective view of a cylinder segment-holding device of the testbench device of the testbench device of FIG. 1.

According to FIG. 4, the fastening device 58 has, further, a cylindrical recess 65 which is formed on the testpiece holder 57, runs in the vertical axis direction z and issues on the underside at the testpiece holder 57 and into which a cylindrical pin 67 projecting upwards from the testpiece stay 59 in the vertical axis direction z can be introduced with a defined radial play. The pin 67 introduced into the recess 65 is in bearing contact with a ball 68 arranged in an upper end region of the recess 65. The radial play and the ball 68 allow simple rotation and pivoting of the testpiece stay 59 in relation to the testpiece holder 57.

The fastening device 58 has, further, two spherical pressure screws 69 which can be screwed into the testpiece holder 57 in which, in the screwed-in state, are in bearing contact by means of their spherical contact face with a circumferentially running wave profile of the cylindrical pin 67, in such a way that the rotational movement of the testpiece stay 59 in relation to the testpiece holder 57 is blocked.

Moreover, the fastening device 58 comprises here further (here, for example, three) spherical pressure screws 73 which can be screwed into the testpiece holder 57 and by means of which the pivoting movement of the testpiece stay 59 can also be blocked. The here, for example, three spherical pressure screws 73 form, as seen from above in the vertical axis direction z, a triangle and, by being screwed into the testpiece holder 57 or by pivoting of the testpiece stay 59 in relation to the testpiece holder 57, can be brought into bearing contact with a planar topside 75 of the testpiece stay 59. The blocking of the pivoting movement of the testpiece stay 59 takes place when all three spherical pressure screws 73 are brought into bearing contact with the topside 75 of the testpiece stay. Depending on the depth to which the spherical pressure screws 73 are screwed in, a pivot angle of the testpiece stay 59 in relation to the testpiece holder 57 can be set.

Compensation of the angular offset between the cylinder segment axis and the piston ring axis takes place by means of a pressing device which presses the cylinder segment-holding device 9 against the piston ring-holding device 5 with a defined pressure force F (FIG. 3). The pressure force F causes a compensating movement of the testpiece stay 59, which is rotatable and pivotable in relation to the testpiece holder 57, or of the cylinder runway segment 12 held on the said testpiece stay and thus makes it possible to produce optimal contact between cylinder runway segment 12 and piston ring 11. After the angular offset has been compensated, the rotatability and pivotability of the testpiece stay 59 in relation to the testpiece holder 57 are blocked.

Figure 7:
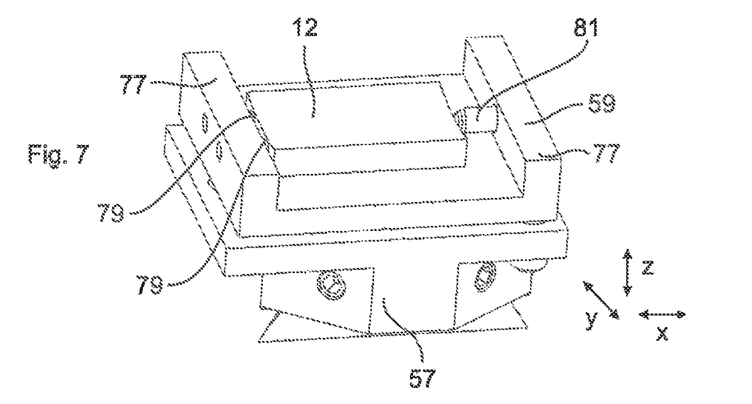
FIG. 7 is a perspective view of a bottom and side of the cylinder segment-holding device according to a first exemplary embodiment.

FIG. 7 shows the U-shaped testpiece stay 59 holding the cylinder runway segment 12. The testpiece stay 59 of U-shaped form has U-legs 77 which are arranged at front and rear in a longitudinal axis direction x and project in the vertical axis direction z and between which the cylinder runway segment 12 can be chucked. The chucking of the cylinder runway segment 12 between the U-legs 77 takes place here, for example, by means of two cylindrical pins 79 inserted into one U-leg 77 and by means of a spherical pressure screw 81 screwed into the other U-leg 77 and pressing the cylinder runway segment 12 against the two cylindrical pins 79.

Furthermore, the cylinder runway segment 12 capable of being chucked between the U-legs 77 can be chucked to the testpiece stay 59 both in a first chucking position and in a second chucking position rotated through 180 degrees about a vertical axis running in the vertical axis direction z. According to FIG. 9, the cylinder runway segment 12 is secured to the testpiece stay 59 in such a way that, as a result of this rotation of the cylinder runway segment 12 through 180 degrees, the friction track having the track width Δx is displaced in the longitudinal axis direction x. Two test runs can thereby be carried out by means of a single cylinder runway segment 12.

Figure 8:
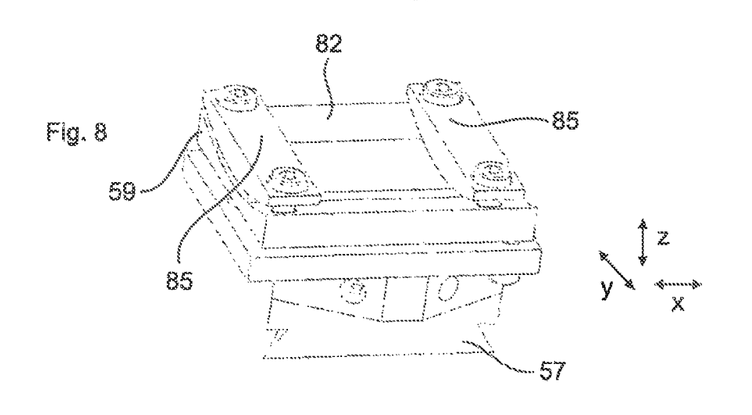
FIG. 8 is a perspective view of a bottom and side of the cylinder segment-holding device according to a second exemplary embodiment.

FIG. 8 shows a second embodiment of the testpiece stay 59. The testpiece stay 59 according to this second embodiment is designed in such a way that a cylinder runway segment 12 manufactured in the manner of a cylinder liner can be secured to it. The testpiece stay 59 has a bearing face 82 which is contour-adapted to the cylinder runway segment 12 and which can be brought into sheet-like bearing contact with that side of the cylinder runway segment 12 which faces away from the piston ring 11. By means of clamping jaws 85, likewise contour-adapted to the cylinder runway segment 12, the cylinder runway segment 12 can be pressed against the bearing face 82.

Furthermore, the cylinder segment-holding device 9 may have a heating foil 87 (FIG. 6) which is chucked between the testpiece holder 57 and the testpiece stay 59 and by means of which the cylinder runway segment 12 can be heated to a defined temperature, for example to about 130° C.

LIST OF REFERENCE SYMBOLS

1 Testbench device
3 Fixing plate
5 Piston ring-holding device
7 Rocker
9 Cylinder segment-holding device
11 Piston ring
12 Cylinder runway segment
13 Piston adaptation
14 Friction track
15 Piston ring groove
17 Adapter element
18 Abutment
19 Reception block
20 Adapter body
21 Inner face piston adaptation
22 Leg
23 Bearing face adapter body
25 Screws
27 Land 29 Topside reception block
33 Cylinder adaptation
37 Recess cylinder adaptation
41 Intermediate plate
45 U-leg intermediate plate
47 U-leg baseplate
49 Baseplate
51 Free space
53 U-base intermediate plate
54 Measuring device
55 U-base baseplate
56 Heating cartridge
57 Testpiece holder
58 Fastening device
59 Testpiece stay
60 Conveying line lubrication device
65 Cylindrical recess
67 Cylindrical pin
68 Ball
69 Spherical pressure screw
73 Spherical pressure screw
75 Topside testpiece stay
77 U-leg testpiece stay
79 Cylindrical pin
81 Spherical pressure screw
82 Bearing face testpiece stay
85 Clamping jaws
87 Heating foil
A Axis
$F_A$ Pressure force
S Pivoting point
$\Delta h$ Height offset
$\Delta x$ Track width

The invention claimed is:

1. A testbench device for the analysis and/or optimization of the tribological properties in a piston ring/cylinder runway system, comprising:
   a cylinder segment-holding device configured to hold a cylinder runway segment as a testpiece;
   a piston ring-holding device having a piston with a ring-shaped outer contour and with at least one circumferentially continuous piston ring groove;
   a piston ring element held on the piston ring-holding device and capable of being brought into bearing contact with the cylinder runway segment, wherein the piston ring element is a piston ring arranged in the circumferentially continuous piston ring groove, wherein the piston ring-holding device includes a cylinder element at least partially surrounding the piston in a circumferential direction and having a cylinder running face in contact with the piston ring element;
   a reception block that prevents relative movement between the cylinder element and the piston; and
   an actuation device configured to actuate at least one of the cylinder runway segment and the piston ring element such that the cylinder runway segment is displaced relative to the piston ring element in at least one defined direction of space.

2. The testbench device according to claim 1, wherein the testbench is a tribometer.

3. The testbench device according to claim 1, wherein the actuation device actuates the at least one of the cylinder runway segment and the piston ring element such that the cylinder runway segment is displaced relative to the piston ring element in an oscillating movement.

4. The testbench device according to claim 1, wherein the piston ring element is guided in the piston ring groove with a defined axial play.

5. The testbench device according to claim 1, wherein the reception block has a measuring device determining a coefficient of friction between the piston ring element and the cylinder runway segment.

6. The testbench device according to claim 1, wherein the cylinder element has a recess providing free access from outside to the piston ring element therein, the recess configured so that the cylinder runway segment held on the cylinder segment-holding device can be brought through the recess into bearing contact with the piston ring element and can be displaced in relation to the piston ring element in the at least one defined direction of space.

7. The testbench device according to claim 1, further comprising a lubrication device configured to deliver a defined quantity of lubricant at least to contact regions of the piston ring element, piston ring groove, and cylinder runway segment.

8. The testbench device according to claim 7, wherein the lubrication device delivers a quantity of lubricant at about 2.5 µl/min.

9. The testbench device according to claim 1, further comprising at least one of a piston heating element heating the piston to a defined temperature of about 350° C., and a cylinder runway segment heating element heating the cylinder runway segment to a defined temperature of about 130° C.

10. The testbench device according to claim 1, further comprising a pressing device configured to press the cylinder runway segment against the piston ring element with a defined pressure force ($F_A$).

11. The testbench device according to claim 1, further comprising a tilting device configured to tilt the cylinder segment-holding device with the piston ring-holding device from a horizontal position to a vertical position, and vice versa, in which case, in the horizontal position, a piston axis running in the piston axial direction runs horizontally and, in the vertical position, the piston axis runs vertically.

12. The testbench device according to claim 1, wherein the piston ring-holding device is held stationary, and the actuation device displaces the cylinder segment-holding device in relation to the stationary piston ring-holding device in the at least one defined direction of space.

13. A testbench device, for the analysis and/or optimization of the tribological properties in a piston ring/cylinder runway system, comprising:
   a cylinder segment-holding device configured to hold a cylinder runway segment as a testpiece;
   a piston ring-holding device having a piston with a ring-shaped outer contour and with at least one circumferentially continuous piston ring groove;
   a piston ring element held on the piston ring-holding device and capable of being brought into bearing contact with the cylinder runway segment, wherein the piston ring element is a piston ring arranged in the circumferentially continuous piston ring groove; and
   an actuation device configured to actuate at least one of the cylinder runway segment and the piston ring element such that the cylinder runway segment is displaced relative to the piston ring element in at least one defined direction of space,
   wherein the piston ring-holding device includes a reception block, the cylinder element and the piston are secured to the reception block, and the reception block has a measuring device determining a coefficient of friction between piston ring element and cylinder runway segment, and wherein the reception block is arranged at least partially in an inner cavity of the piston designed as a hollow piston, the reception block being secured to the piston by an adapter element arranged between reception block and the piston.

14. The testbench device according to claim 13, further comprising a piston heating element secured to the reception block such that heating warmth of the piston heating element passes into the piston via the reception block and the adapter element.

15. A testbench device for the analysis and/or optimization of the tribological properties in a piston ring/cylinder runway system, comprising:
- a cylinder segment-holding device configured to hold a cylinder runway segment as a testpiece;
- a piston ring-holding device having a piston with a ring-shaped outer contour and with at least one circumferentially continuous piston ring groove;
- a piston ring element held on the piston ring-holding device and capable of being brought into bearing contact with the cylinder runway segment, wherein the piston ring element is a piston ring arranged in the circumferentially continuous piston ring groove; and
- an actuation device configured to actuate at least one of the cylinder runway segment and the piston ring element such that the cylinder runway segment is displaced relative to the piston ring element in at least one defined direction of space;
- wherein the cylinder segment-holding device has a testpiece holder and a testpiece stay secured to the testpiece holder, the testpiece stay being configured to secure the cylinder runway segment, and a blocking device selectively blocking and releasing at least one of pivoting and rotation of the testpiece stay in relation to the testpiece holder, the testpiece stay being secured to the testpiece holder at least one of pivotably and rotatably, in such a way that an angular offset between a cylinder segment axis running in the an axial direction of the cylinder runway segment and a piston ring element axis running in the an axial direction of the piston ring element can be at least one of compensated and set.

16. The testbench device according to claim 15, wherein the blocking device has at least one screw element threadably insertable into one of the testpiece holder and the testpiece stay to block at least one of pivoting and rotation.

17. The testbench device according to claim 15, wherein the testpiece stay is U-shaped with U-legs, the cylinder runway segment is manufactured particularly in the manner of a cylinder crankcase and is arranged between the U-legs of the testpiece stay and secured to the U-legs of the testpiece stay.

18. The testbench device according to claim 15, wherein the testpiece stay has a bearing region contour-adapted to a side of the cylinder runway segment facing away from the piston ring element, and the testbench device includes at least one clamping element configured to clamp the cylinder runway segment against the bearing region to secure the cylinder runway segment to the testpiece stay.

19. The testbench device according to claim 15, further comprising a pressing device configured to press the cylinder runway segment against the piston ring element with a defined pressure force ($F_A$), and wherein the cylinder segment-holding device is configured so that at least one of setting and compensation of the angular offset takes place by the cylinder runway segment being pressed against the piston ring element with the defined pressure force ($F_A$).

20. The testbench device according to claim 19, wherein the testpiece holder has a cylindrical recess in which a cylindrical pin of the testpiece stay is guided with a radial play enabling the angular offset to be at least one of compensated and set.

21. A testbench device for the analysis and/or optimization of the tribological properties in a piston ring/cylinder runway system, comprising:
- a cylinder segment-holding device configured to hold a cylinder runway segment as a testpiece;
- a piston ring-holding device having a piston with a ring-shaped outer contour and with at least one circumferentially continuous piston ring groove;
- a piston ring element held on the piston ring-holding device and capable of being brought into bearing contact with the cylinder runway segment, wherein the piston ring element is a piston ring arranged in the circumferentially continuous piston ring groove; and
- an actuation device configured to actuate at least one of the cylinder runway segment and the piston ring element such that the cylinder runway segment is displaced relative to the piston ring element in at least one defined direction of space;
- wherein the cylinder runway segment is arranged above the piston ring element in a vertical axis direction (z), and in that the cylinder runway segment can be brought at a bearing region into bearing contact with the piston ring element, the cylinder runway segment being secured to the cylinder segment-holding device by a testpiece stay in such a way that the bearing region is displaced in the axial direction of the cylinder runway segment as a result of the rotation of the cylinder runway segment through 180° about an axis (A) running in the vertical axis direction (z).

* * * * *